(12) United States Patent
Tozer (10) Patent No.: US 7,204,957 B2
(45) Date of Patent: Apr. 17, 2007

(54) SANITIZABLE CUSHIONED SHEATH FOR THE HANDLE OF A CULINARY KNIFE OR SIMILAR ARTICLE

(76) Inventor: Jason Grant Tozer, 355 S. Robertson Blvd., Beverly Hills, CA (US) 90211

( * ) Notice: Subject to any disclaimer, the term of this patent is extended or adjusted under 35 U.S.C. 154(b) by 0 days.

(21) Appl. No.: 11/172,699

(22) Filed: Jun. 30, 2005

(65) Prior Publication Data

US 2006/0000322 A1    Jan. 5, 2006

Related U.S. Application Data

(60) Provisional application No. 60/584,926, filed on Jun. 30, 2004.

(51) Int. Cl.
*A61L 2/00* (2006.01)
*B26B 29/02* (2006.01)
*A47L 25/00* (2006.01)

(52) U.S. Cl. ............................. 422/28; 30/143; 30/151; 30/340; 606/167; 606/178; 604/22; 15/218; 15/218.1; 206/363

(58) Field of Classification Search .................. 30/340, 30/341, 342, 343, 344; 16/441, 413, 423, 16/422, 110.1, 435, 904; 422/300, 28, 26, 422/39, 41, 42; 81/489; 206/233, 209, 15.2, 206/15.3, 363, 349, 225, 253; 248/905; 606/167, 606/17, 178, 170, 176, 177; 604/22; 15/210.1, 15/218, 144.3, 160, 104.94, 257.01, 218.1
See application file for complete search history.

(56) References Cited

U.S. PATENT DOCUMENTS

| | | | | |
|---|---|---|---|---|
| 181,764 A * | 9/1876 | Barker | ...................... | 15/218.1 |
| 487,446 A * | 12/1892 | Murphy | ..................... | 15/218.1 |
| 566,944 A * | 9/1896 | Stalker | ....................... | 15/218.1 |
| 1,491,780 A * | 4/1924 | Abbott | ........................ | 292/347 |
| 2,073,137 A * | 3/1937 | Bimrose | ..................... | 433/116 |
| 2,635,274 A * | 4/1953 | Hatcher et al. | ............ | 15/147.1 |
| 2,648,858 A * | 8/1953 | Paull | ............................ | 15/118 |
| 2,816,312 A * | 12/1957 | Beck et al. | ................. | 15/210.1 |
| 3,495,918 A * | 2/1970 | Leland | ........................ | 401/201 |
| 3,723,061 A * | 3/1973 | Stahl | ........................... | 206/370 |

(Continued)

*Primary Examiner*—Kenneth E. Peterson
*Assistant Examiner*—Ghassem Alie
(74) *Attorney, Agent, or Firm*—John M. May (57) ABSTRACT

A handle-sheath may be molded for of a flexible material and may be shaped and dimensioned so as to be stretched over a conventional handle, thereby permitting the sheath to be conveniently removed and replaced. An internal flushing mechanism is preferably provided for sanitizing the interior of the sheath without requiring the sheath to be removed from the handle. The handle sheath may be molded from a tear-resistant, soft touch, elastic polymer such as thermoplastic elastomer (otherwise known as "TPE"). The interior may be provided with inwardly facing support studs and/or channel walls which define a plurality of individual-contact areas between the sheath and the handle, each of which providing a respective localized intimate contact area for frictionally securing the sheath to the handle, and at the same time defining channels which facilitate the maintenance of a sanitary condition between the handle sheath and the underlying structure, as will be described in more detail hereinafter. The sheath is preferably provided with one or more attachment points to which may be attached a loop or strap adapted to be gripped by the user as the sheath is being installed or removed onto the knife handle, and/or which may secure the user's hand to the knife during use.

6 Claims, 7 Drawing Sheets

U.S. PATENT DOCUMENTS

| | | | |
|---|---|---|---|
| 4,046,254 A * | 9/1977 | Kramer | 206/370 |
| 4,362,241 A * | 12/1982 | Williams | 206/210 |
| 4,374,445 A * | 2/1983 | Wilson | 15/220.4 |
| 4,377,035 A * | 3/1983 | Dalichow | 30/147 |
| 4,704,760 A * | 11/1987 | Grieshaber | 15/218.1 |
| 4,736,842 A * | 4/1988 | Uetake et al. | 206/363 |
| 5,447,684 A * | 9/1995 | Williams | 422/20 |
| 5,471,705 A * | 12/1995 | Dao | 15/236.05 |
| 5,569,282 A * | 10/1996 | Werner | 606/167 |
| 5,797,943 A * | 8/1998 | Danks et al. | 606/185 |
| 6,099,813 A * | 8/2000 | Gipson, II | 422/300 |
| 6,295,688 B1 * | 10/2001 | Sayles et al. | 15/210.1 |
| 6,331,088 B2 * | 12/2001 | Owens | 401/282 |
| 6,546,594 B1 * | 4/2003 | Wills | 16/422 |
| 6,793,882 B1 * | 9/2004 | Verschuur | 422/6 |
| 2001/0039428 A1 * | 11/2001 | Dinger et al. | 606/167 |
| 2002/0054784 A1 * | 5/2002 | Wolf | 401/282 |
| 2002/0127139 A1 * | 9/2002 | Lidahl et al. | 422/28 |
| 2004/0221410 A1 * | 11/2004 | Padula | 15/210.1 |
| 2005/0025665 A1 * | 2/2005 | Raniwala | 422/28 |
| 2005/0138748 A1 * | 6/2005 | Cisneros | 15/210.1 |
| 2006/0059663 A1 * | 3/2006 | D'Ambrosio | 16/441 |

* cited by examiner

SANITIZABLE CUSHIONED SHEATH FOR THE HANDLE OF A CULINARY KNIFE OR SIMILAR ARTICLE

TECHNICAL FIELD

The present invention relates generally to culinary implements such as cutlery and more particularly to a sanitizable handle-sheath that provides a user with enhanced comfort and support.

BACKGROUND

Conventional chef knifes have relatively rigid handles made of a relatively durable material such as wood or ABS. More recently so called "soft grip" handles have become commercially available which better conform to a user's hand, thereby providing enhanced support and comfort. However, the: "soft" portion of such a handle is less durable than a conventional handle and is prone to separations, abrasion and cracking, especially when subjected to the high temperatures and caustic liquids conventionally used to clean and sanitize culinary implements prior to use. Moreover, any resultant abrasions or cracks in the soft grip material could trap blood, fat and other contaminants, rendering the knife no longer usable.

The United States Food and Drug Administration ("FDA") and the National Sanitation Foundation ("NSF") have promulgated standards for materials and procedures for maintaining sanitary conditions in a commercial kitchen or other food processing environment.

TECHNICAL OVERVIEW

In accordance with one aspect of the invention, a handle-sheath is molded of a flexible material and is shaped and dimensioned so as to be stretched over a conventional handle, thereby permitting the sheath to be conveniently removed and replaced. In accordance with another aspect which may be practiced independently of the first, the handle sheath is provided with an internal flushing mechanism for sanitizing the interior of the sheath without requiring it be removed from the handle. These different aspects of the invention are particularly advantageous in a commercial environment such as a restaurant or food processing plant, in which comfort, support, convenience, durability and sanitation are all highly desirable.

In one presently preferred embodiment, the handle sheath is molded from a tear-resistant, soft touch, elastic polymer such as thermoplastic elastomer (otherwise known as "TPE"). The interior may be provided with inwardly facing support studs and/or channel walls which define a plurality of individual contact areas between the sheath and the handle, each of which providing a respective localized intimate contact area for frictionally securing the sheath to the handle, and at the same time defining channels which facilitate the maintenance of a sanitary condition between the handle sheath and the underlying structure, as will be described in more detail hereinafter. The sheath is preferably provided with one or more attachment points to which may be attached a loop or strap adapted to be gripped by the user as the sheath is being installed or removed onto the knife handle, and/or which may secure the user's hand to the knife during use.

BRIEF DESCRIPTION OF DRAWINGS

The invention may be better understood by reference to the appended drawings of one or more specific embodiments thereof, in which:

FIG. 3 comprising

FIG. 4 comprising

FIG. 5 comprising

DETAILED DESCRIPTION OF CERTAIN PREFERRED EMBODIMENTS

Figure 1:
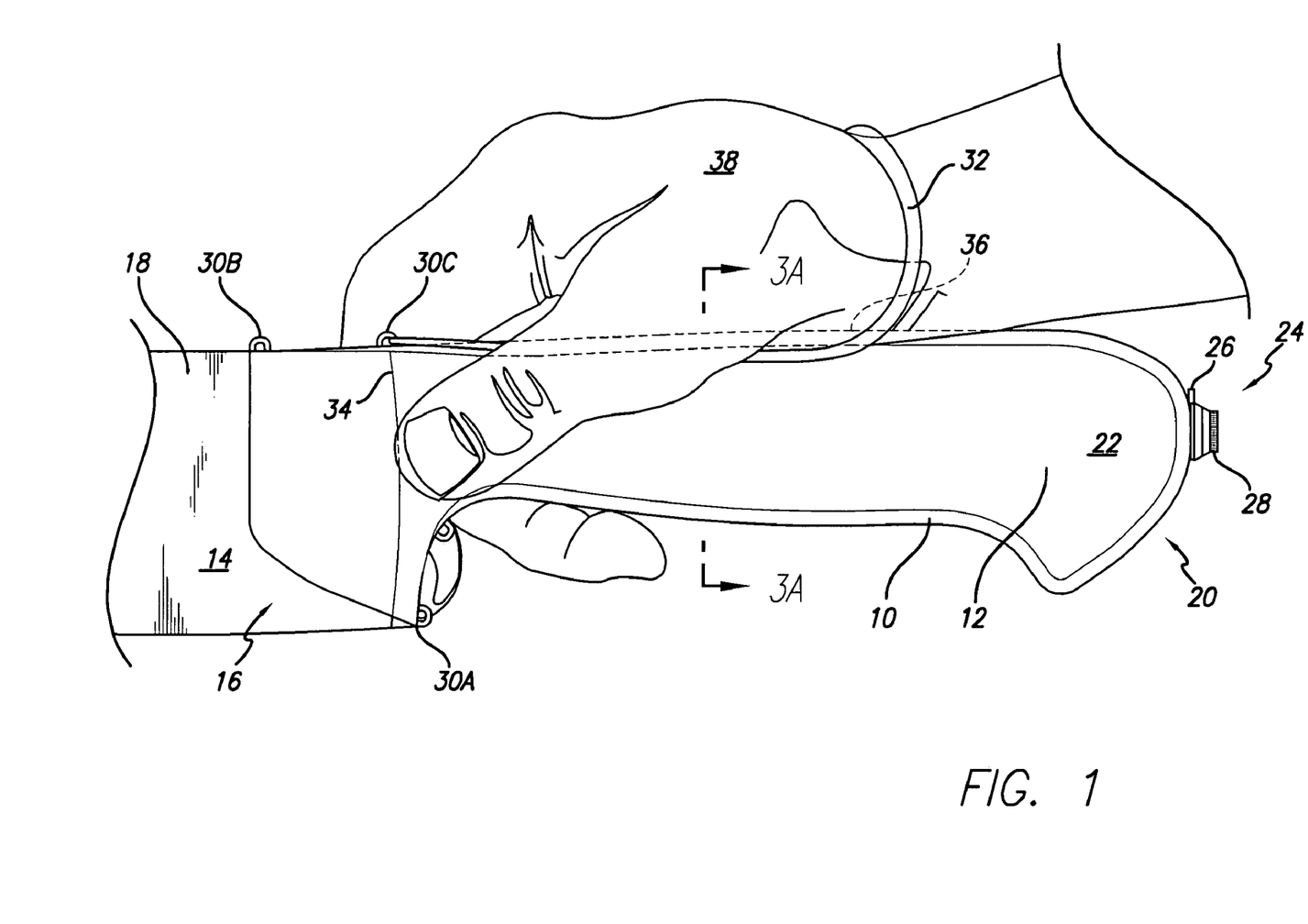
FIG. 1 shows one embodiment of a soft touch handle sheath in use in its operative installed position on the handle of an exemplary chef's knife.
Figure 2:
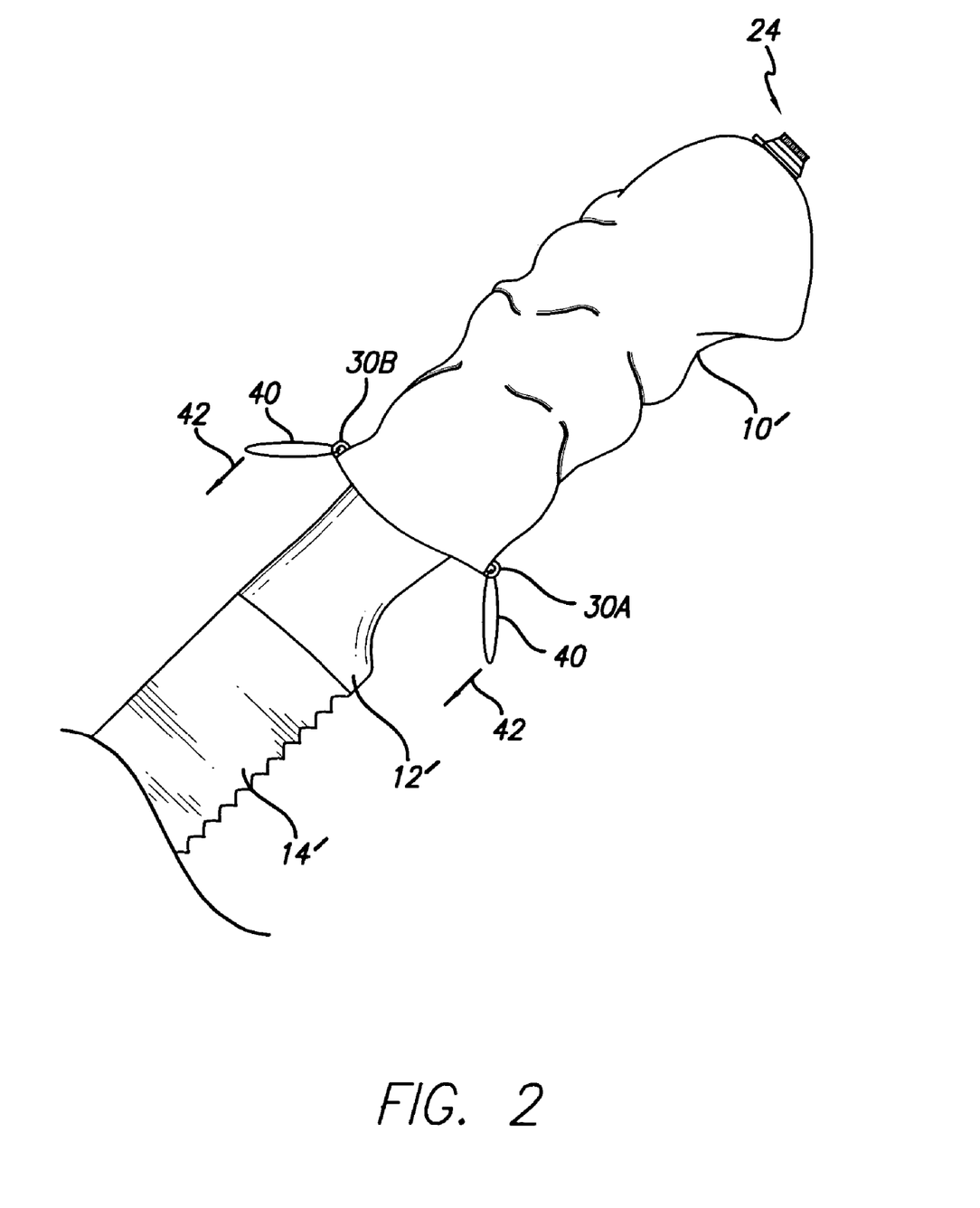
FIG. 2 shows a second embodiment of a soft touch handle sheath as it is being installed onto the handle of an exemplary serrated knife.

Reference should now be made to FIG. 1, which shows one embodiment of a soft touch handle sheath 10 in use its operative installed position on the handle 12 of an exemplary chef's knife 14. Sheath 10 is generally in the shape of an elongated casing, with an open end 16 adjacent the blade portion 18 of handle 12, and a closed end 20 at the remote end 22 of handle 12. A flushing plug 24 comprising a body portion 26 and a closure portion 28 (see also FIG. 5A and FIG. 5B) is provided at the end of handle 12 remote from blade 20, the purpose of which will be hereinafter explained with reference to FIG. 4 and FIG. 6. Sheath 10 is preferably provided with one or more attachment rings 30A, 30B, 30C. As shown, a wrist strap 32 is secured to attachment ring 30C at an intermediate point 34 along the upper edge 36 of sheath 10 and is used to secure the user's hand 38 to the handle 12, while attachment rings 30A, 30B at the open end 16 may be used (as shown in FIG. 2) to pull the sheath 10 on to (or off from) handle 12. Support strap 32 not only protects the user from accidental slippage of the knife handle 12 from the user's hand 38, but also provides the user with enhanced conformability and comfort in the form of a more stable support for the hand of the user with reduced shock to the wrist joint, and with a refined cutting technique as a result of the improved poise and reduced wrist rollover.

Sheath 10 is preferably injection molded of a transparent, light weight, soft touch FDA and NSF compliant thermoplastic elastomer having superior tear resistance and a relatively low durometer measure of about 30 Shore A or 30 Shore 00, such as is available from GLS Corporation.

FIG. 2 shows a second embodiment of a soft touch handle sheath 10' as it is being installed onto the handle 12' of an exemplary serrated knife 14'. In particular, it will be seen that a pair of loops 40 are attached to respective attachment rings 30B, 30A to facilitate transfer of a stretching force 42 to the sheath 10.

Figure 3A:
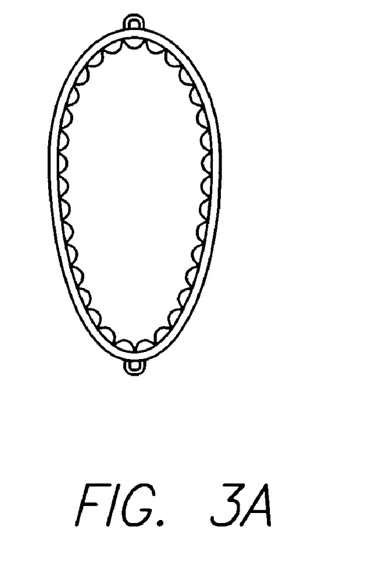
FIG. 3A, FIG. 3B, and FIG. 3C, are detailed views of the interior of an exemplary handle sheath showing inwardly protruding studs which define a plurality of flushing channels.
Figure 3B:
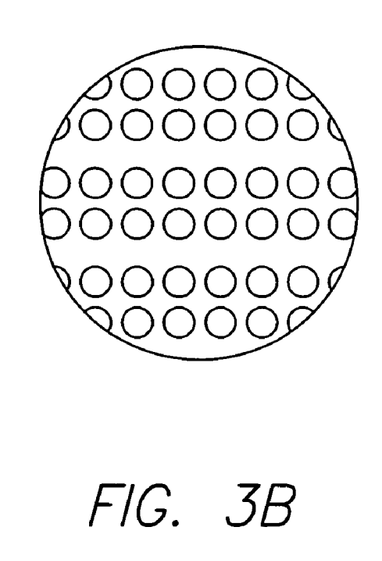
Figure 3C:
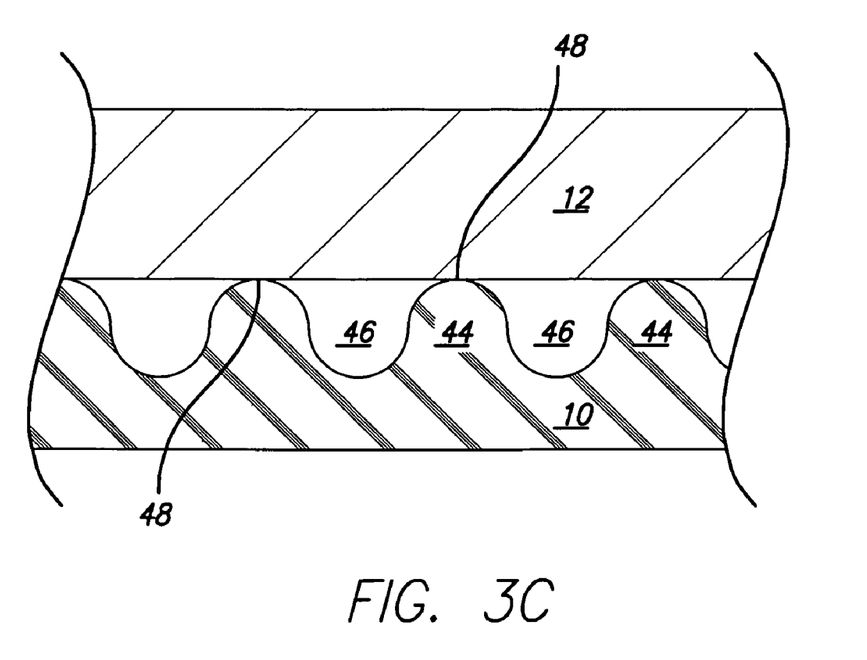

FIG. 3 comprising FIG. 3A, FIG. 3B, and FIG. 3C are more detailed conceptual views of the interior of an exemplary knife sheath 10 showing inwardly protruding studs or ribs 44 which define a plurality of flushing channels 46 which facilitate the maintenance of a sanitary condition between the handle sheath 10 and the underlying rigid handle 12. Studs or ribs 44 also function to define a plurality of individual contact areas 48 between the sheath 10 and the handle 12, each of which provide intimate frictional contact for better securing the sheath 10 to the handle 12.

Figure 4A:
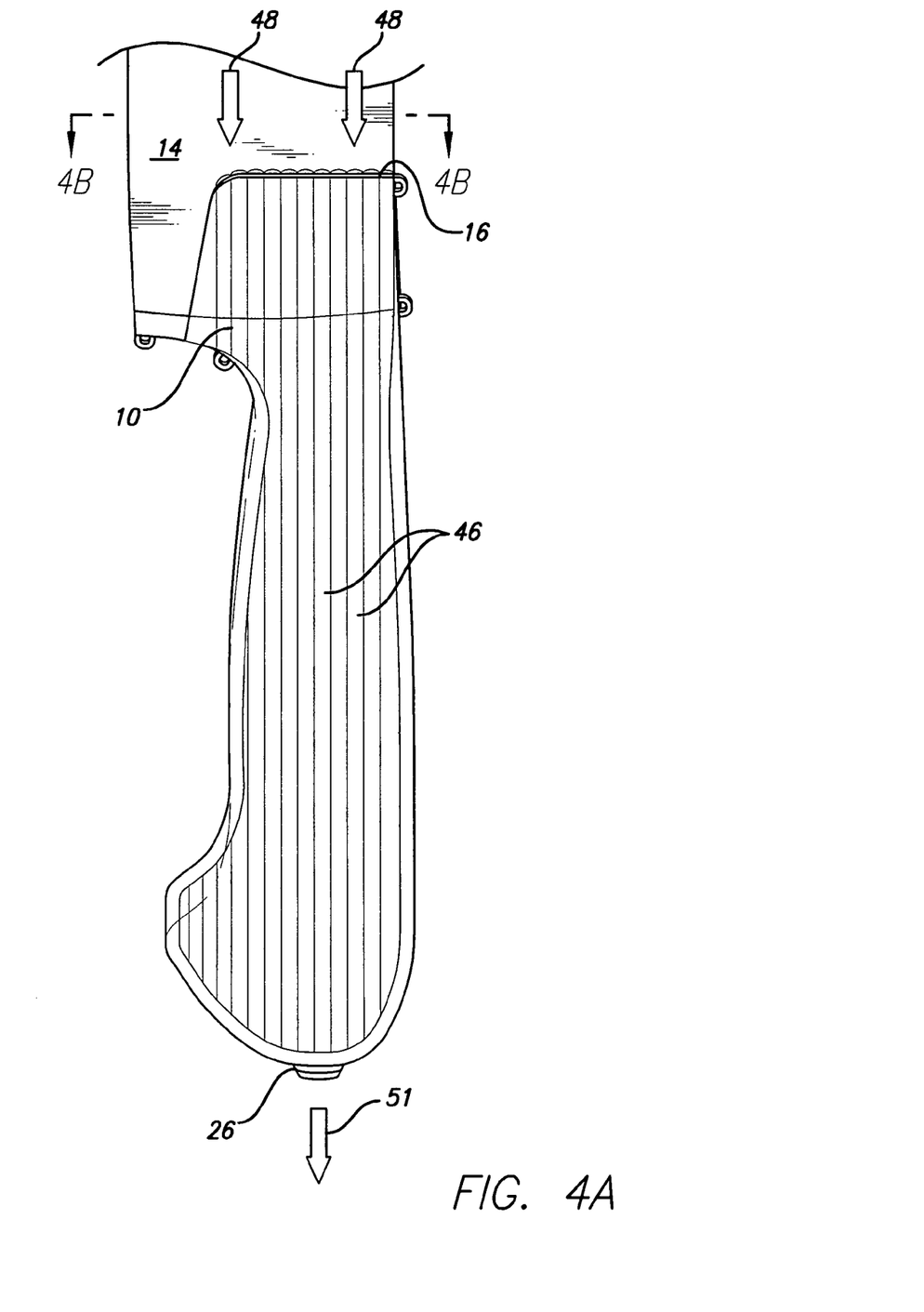
FIG. 4A, FIG. 4B show how channels formed on an interior surface of the sheath of FIG. 3 may be used to introduce a sanitizing fluid.
Figure 4B:
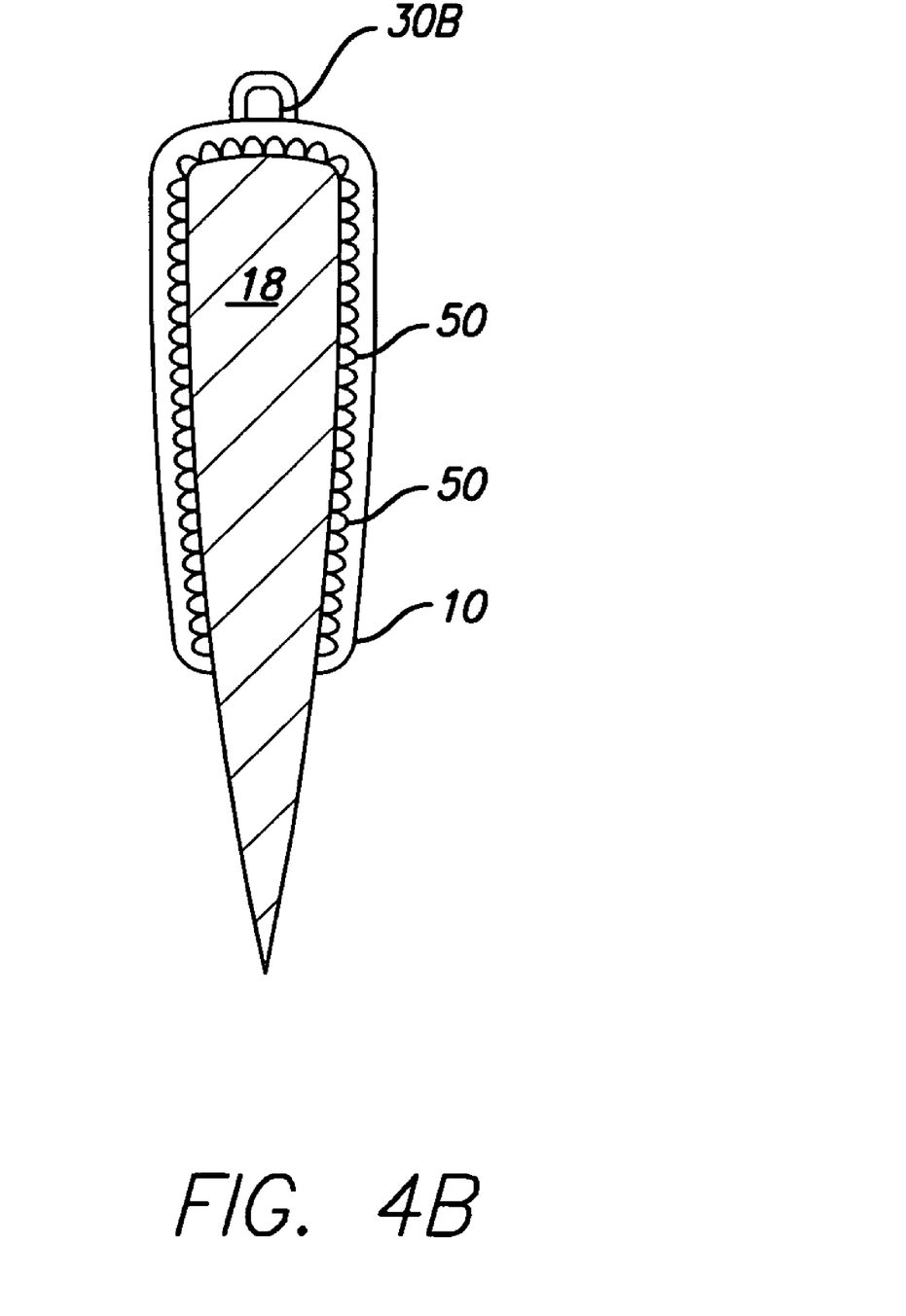

FIG. 4 show how the channels 46 (see also FIG. 3C) formed on an interior surface of the sheath 10 provide fluid communication between the open end 16 and the flushing plug body 26. In particular, a sanitizing fluid (such as chorine bleach) may be introduced (arrow 48) into the exposed channel openings 50 (see FIG. 4B) at open end 16, and, upon removal of flush plug closure portion 28 (see FIG. 1) may exit (arrow 51) from flush plug body portion 26 at the closed end 20.

Figure 5A:
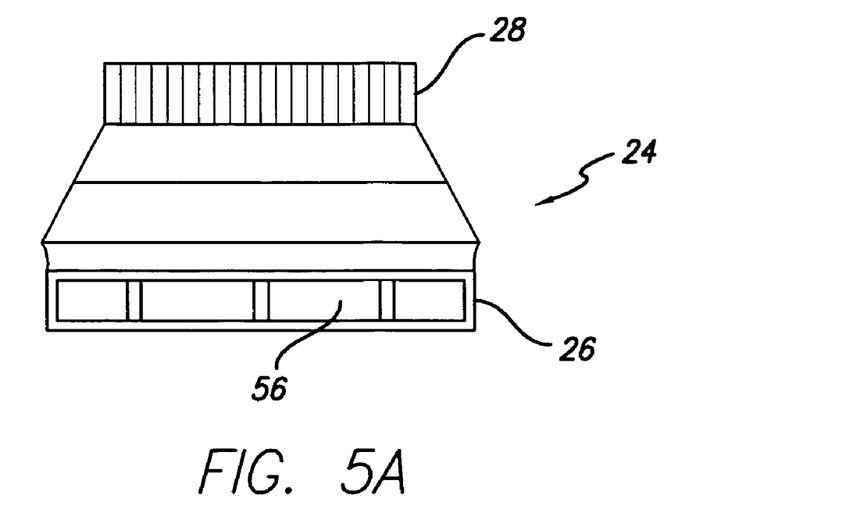
FIG. 5A and FIG. 5B are respective closed and open detailed views of the flushing plug fixtures shown in FIG. 1 and FIG. 2.
Figure 5B:
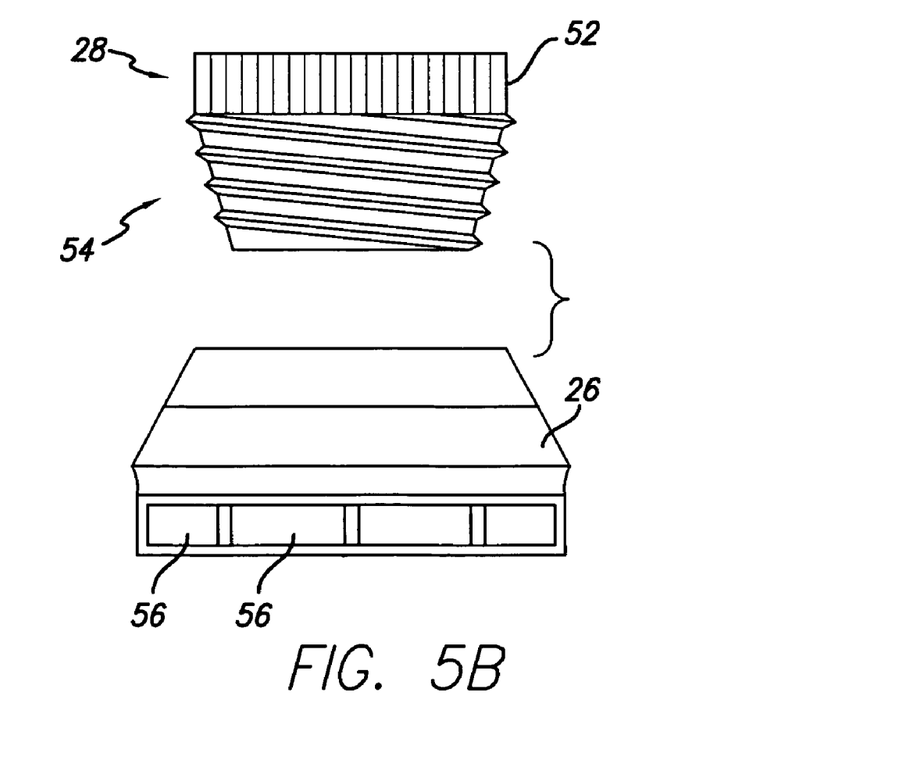

FIG. 5 comprising FIG. 5A and FIG. 5B are respective detailed view of the flushing plugs 24 shown in FIG. 1 and FIG. 2. In particular, it may be seen that closure portion 28 is preferably provided with a knurled exposed knob 52 and a threaded portion 54, while body portion includes a plurality of transverse fluid openings 56 adapted to maintain fluid communication with the channels 46.

Figure 6:
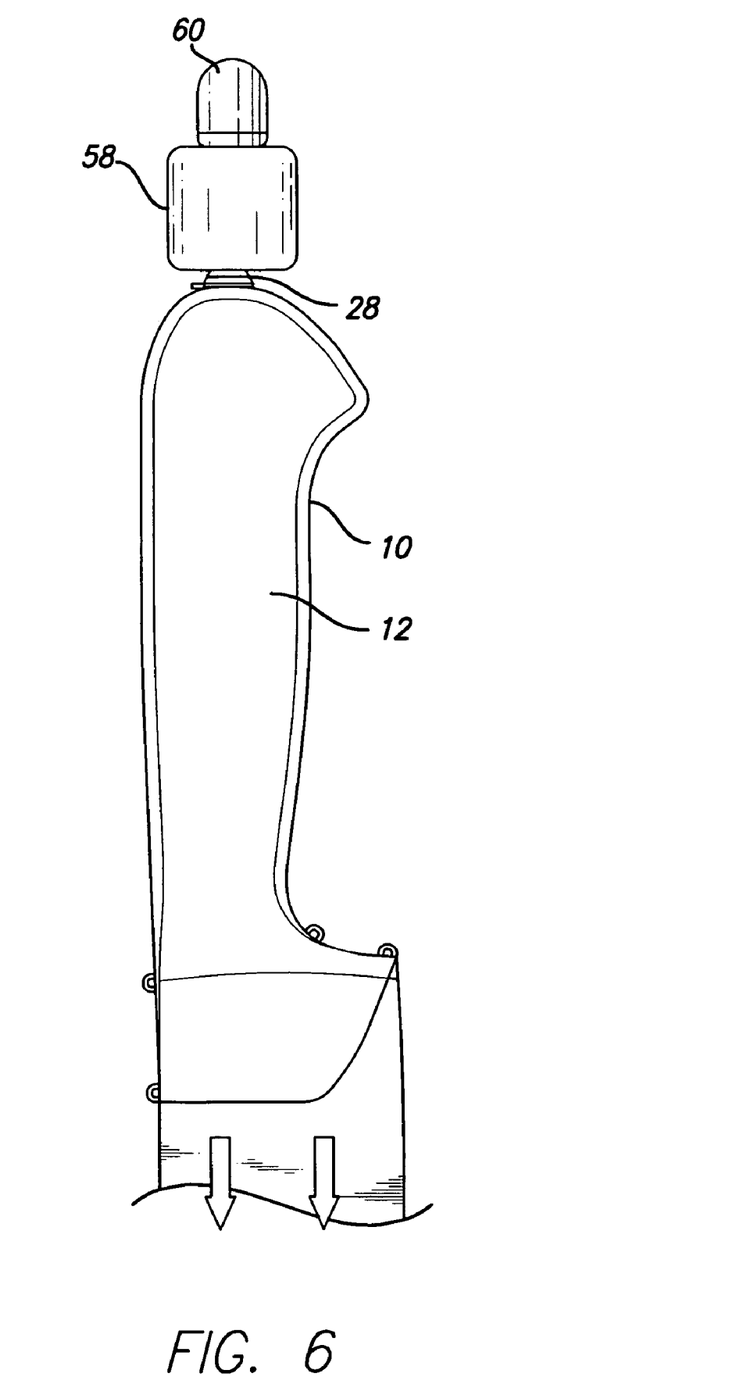
FIG. 6 shows an optional sanitizing cartridge connected between a flushing plug receptacle and a source of pressurized fluid.

FIG. 6 shows an optional sanitizing cartridge 58 connected between the flushing plug closure portion 28 and a faucet 60 or other source of pressurized water. Cartridge 58 is preferably preloaded with a slowly dissolving oxidizing agent (for example, a tablet formulation of stabilized chorine) for providing a measured dose of a sanitizing liquid when attached to faucet 60.

While the invention has been described with reference to certain presently preferred embodiments and environments, those skilled in the art will understand that its underlying principles are also applicable to other applications. Accordingly, the scope of the invention is not limited by the described examples, but only by what is set forth in the appended claims. Moreover, these claims are intended to embrace not only the specific structures and steps recited, but also any equivalent structures or steps that are now or may in the future become known to the skilled artisan.

The invention claimed is:

1. A method for sanitizing a culinary tool, comprising:
   installing a soft touch sheath about a rigid handle,
   introducing a liquid between the sheath and the handle, and
   draining the liquid while the sheath is still installed on the handle,
   wherein the handle has a blade end and a remote end and the sheath extends from the blade end to the remote end;
   wherein the sheath has an open end and a closed end, and the installing comprises stretching the open end of the sheath over the handle from the remote end to the blade end; and
   wherein the introducing and draining steps comprise defining a plurality of flushing channels in an interior surface of the sheath from the open end to the closed end to provide fluid communication along an exterior surface of the handle between the blade end and the remote end of the handle when the sheath is stretched over the handle.

2. The method of claim 1 wherein the liquid includes a chemical disinfectant.

3. The method of claim 2 wherein the chemical disinfectant is dispensed from a cartridge operatively connected between the sheath and a pressurized source of water.

4. The method of claim 1 wherein the sheath comprises a removable flush plug adjacent the remote end and the liquid is introduced by gravity at the blade end and is drained from the flush plug.

5. The method of claim 1 wherein the sheath comprises a removable flush plug adjacent the remote end and the liquid is introduced under pressure into the flush plug and is drained at the blade end.

6. The method of claim 1 further comprising the step of frictionally securing the sheath to the handle by means of intimate contact between said handle and at least some of said interior surface portions.

* * * * *